(12) United States Patent
Tingey et al.

(10) Patent No.: US 6,866,656 B2
(45) Date of Patent: Mar. 15, 2005

(54) LUBRICIOUS COATING FOR A MEDICAL DEVICE

(75) Inventors: Kevin Tingey, Sandy, UT (US); Steven W. Johnson, Lehi, UT (US); E. Robert Purdy, Fruit Heights, UT (US); Douglas P. Orr, Sandy, UT (US); Min-Shiu Lee, Escondido, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 384 days.

(21) Appl. No.: 10/056,417

(22) Filed: Jan. 24, 2002

(65) Prior Publication Data

US 2002/0168530 A1 Nov. 14, 2002

Related U.S. Application Data

(60) Provisional application No. 60/263,882, filed on Jan. 24, 2001.

(51) Int. Cl.[7] .......................... A61M 25/00; A61L 29/08
(52) U.S. Cl. ....................... 604/265; 604/256; 604/283
(58) Field of Search ......................................... 604/265

(56) References Cited

U.S. PATENT DOCUMENTS

| | | | |
|---|---|---|---|
| 5,067,491 A | 11/1991 | Taylor, II et al. ............ 128/748 |
| 5,409,471 A | 4/1995 | Atkinson et al. ............ 604/289 |
| 5,425,710 A | 6/1995 | Khair et al. .................. 604/96 |
| 5,540,661 A * | 7/1996 | Tomisaka et al. ............ 604/265 |
| 5,609,629 A * | 3/1997 | Fearnot et al. .............. 623/1.42 |
| 5,669,930 A * | 9/1997 | Igarashi ....................... 606/191 |
| 5,824,049 A * | 10/1998 | Ragheb et al. .............. 623/1.44 |
| 5,834,005 A | 11/1998 | Usala .......................... 424/424 |
| 5,873,904 A * | 2/1999 | Ragheb et al. .............. 623/1.13 |
| 6,096,070 A * | 8/2000 | Ragheb et al. .............. 623/1.39 |
| 6,127,320 A | 10/2000 | Van Ooij et al. ............ 508/138 |
| 6,176,849 B1 * | 1/2001 | Yang et al. .................. 604/265 |
| 6,261,282 B1 | 7/2001 | Jepson et al. ............... 604/533 |
| 6,299,604 B1 * | 10/2001 | Ragheb et al. .............. 604/265 |
| 6,340,465 B1 * | 1/2002 | Hsu et al. .................... 424/400 |
| 6,379,691 B1 * | 4/2002 | Tedeschi et al. ............ 424/423 |
| 6,645,483 B2 * | 11/2003 | McGhee .................. 424/78.08 |
| 6,645,518 B2 * | 11/2003 | Tedeschi et al. ............ 424/423 |
| 6,716,895 B1 * | 4/2004 | Terry .......................... 523/122 |
| 6,730,064 B2 * | 5/2004 | Ragheb et al. .............. 604/265 |

FOREIGN PATENT DOCUMENTS

| | | |
|---|---|---|
| EP | 0 679 373 A2 | 11/1995 |
| EP | 0 716 834 A1 | 6/1996 |
| WO | WO 95/04564 | 2/1995 |
| WO | WO 98/17331 | 4/1998 |
| WO | WO 00/10622 | 3/2000 |

OTHER PUBLICATIONS

PCT International Search Report.

* cited by examiner

*Primary Examiner*—Ellen M. McAvoy
(74) *Attorney, Agent, or Firm*—Mony B. Ghose

(57) ABSTRACT

A lubrication system is disclosed which minimizes friction and that is useful for application on the surface of a flexible portion of a medical device. Such a lubrication system includes a lubricant that is able to move when the flexible portion of the medical device flexes and is biocompatible and is not degraded by the application of alcohol or other conventional medical sterilizing and cleaning agents. The lubricant is bonded to the surface of the flexible portion of the medical device. The lubrication system may be used on an elastomeric septum, such as a silicone rubber elastomer. The lubricant coating may be any type of coating that can be chemically bonded to the elastomer, such as di-paraxylene, poly-(p-xylene), polytetrafluoroethylene, or polyvinylpyrrolidone.

20 Claims, 3 Drawing Sheets

LUBRICIOUS COATING FOR A MEDICAL DEVICE

This application claims the benefit of U.S. Provisional application Ser. No. 60/263,882, which was filed on Jan. 24, 2001, the disclosure of which is herein incorporated by reference.

BACKGROUND OF THE INVENTION

The present invention relates to a lubricious coating that may be applied to a flexible portion of a device such as a medical device to minimize friction.

In many contexts in the medical field it is desirable to provide a device that includes a flexible portion as part of the device. For example, portions of certain medical devices may be flexible to facilitate the insertion of the medical device into a patient and to maximize patient comfort. In addition, elastomeric septums are frequently used on medical devices because they are resilient and flexible and can be used to selectively open and close a passageway. In particular, the open proximal end of a rigid catheter hub may include an elastomeric septum through which another medical device such as a guidewire or an introducer needle may extend. When the guidewire or introducer needle is removed, the septum closes to seal the proximal end of the catheter hub and prevents fluid from escaping from or entering into the catheter hub. In addition, septums may be used in medical valves. The septum is located in the rigid valve body or housing to selectively open and close the valve to fluid flow. In certain valve designs, a needle from a syringe may be inserted through the septum to access the valve. In other valve designs, the male luer end of a syringe is all that is needed to access the valve. The male luer end can either be inserted through a preformed slit in the septum or the male luer end can move the septum in some manner to open and close the valve to fluid flow.

One problem that is encountered in devices of this type is the friction that exists between the flexible portion of the medical device and the patient or another medical device that is used in conjunction with the medical device having the flexible portion. In some circumstances, the friction may be sufficiently large that it is extremely uncomfortable for the patient or extremely difficult for a clinician to operate the medical device. In other circumstances, the friction may even prevent the medical device from working for its intended purpose. Accordingly, a need exists for a lubrication system that may be used on flexible portions of medical devices to minimize friction against the flexible portion. Such a lubrication system must include a lubricant that is able to move when the flexible portion flexes. In addition, the lubricant must be biocompatible and must not be degraded by application of alcohol or other conventional medical sterilizing and cleaning agents that are typically used with medical devices. The lubricant should be permanently associated with the elastomeric component so that it will perform throughout the life of the medical device.

SUMMARY OF THE INVENTION

It is therefore an object of an aspect of this invention to provide a lubrication system that may be used on flexible portions of medical devices to minimize friction.

It is another object of an aspect of this invention to provide a lubrication system that includes a lubricant that moves when the flexible portion flexes.

It is yet another object of an aspect of this invention to provide a lubrication system that is biocompatible and is not degraded by the application of alcohol or other conventional medical sterilizing and cleaning agents.

The lubrication system of the present invention includes a lubricant that is coated onto the surface of the flexible portion of the medical device that is to be treated. The lubricant is preferably a polymeric material polymerized by vapor deposition on the surface of the flexible portion of the medical device. Examples of acceptable lubricants include di-paraxylene, poly-(p-xylene), polyvinylpyrrolidone, and polytetrafluoroethylene. The lubricant is applied in a very thin layer between specific ranges, thick enough to ensure adequate coverage of the flexible portion of the medical device, but not so thick that the coating would flake off when the flexible portion is deformed. The thickness of the lubricant coating may vary but coatings in the range of from about 0.5 microns to about 1.5 microns in thickness are often acceptable, with coatings in the range of from about 0.75 microns to about 1.25 microns in thickness being more often preferred for most medical applications. Further, coatings of 0.5 to 0.9 microns are preferred for use on the septums of needleless valves and luer access ports, as discussed herein. In any event, the coating is applied in a layer much thinner than coatings of such materials have been applied on medical devices previously.

BRIEF DESCRIPTION OF THE DRAWINGS

The preferred embodiments of the invention are illustrated in the drawings in which like reference numerals refer to like elements and in which.

DETAILED DESCRIPTION OF THE INVENTION

The lubricious coating of this invention is preferably any one of several polymer materials that can be securely applied to the surface of a medical device. Currently, it is envisioned that the coating be applied to the elastomeric septums of needleless valves, such as that disclosed in U.S. Pat. No. 5,540,661, incorporated herein by reference. As would be appreciated by one skilled in the art, the coating of the instant invention may be employed advantageously in connection with other needleless luer access connectors, such as that depicted in FIGS. 1–3, and with other medical devices having flexible surfaces.

Figure 1:
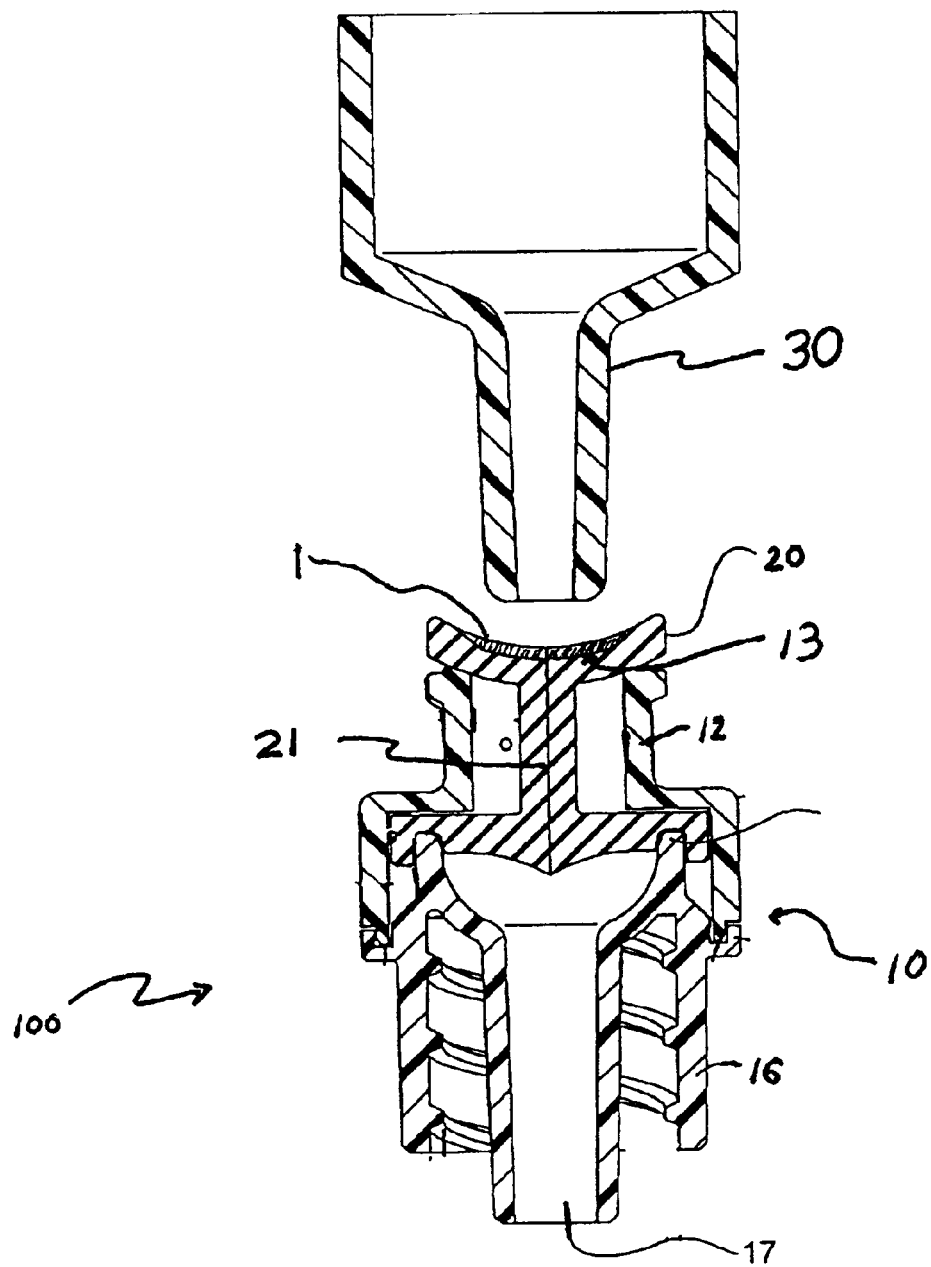
FIG. 1 is a cross sectional view of a needleless luer access connector in a closed position and with a male luer taper of another medical device, such as a syringe, poised for penetration of the connector, the coating of the instant invention being applied to the access connector.
Figure 2:
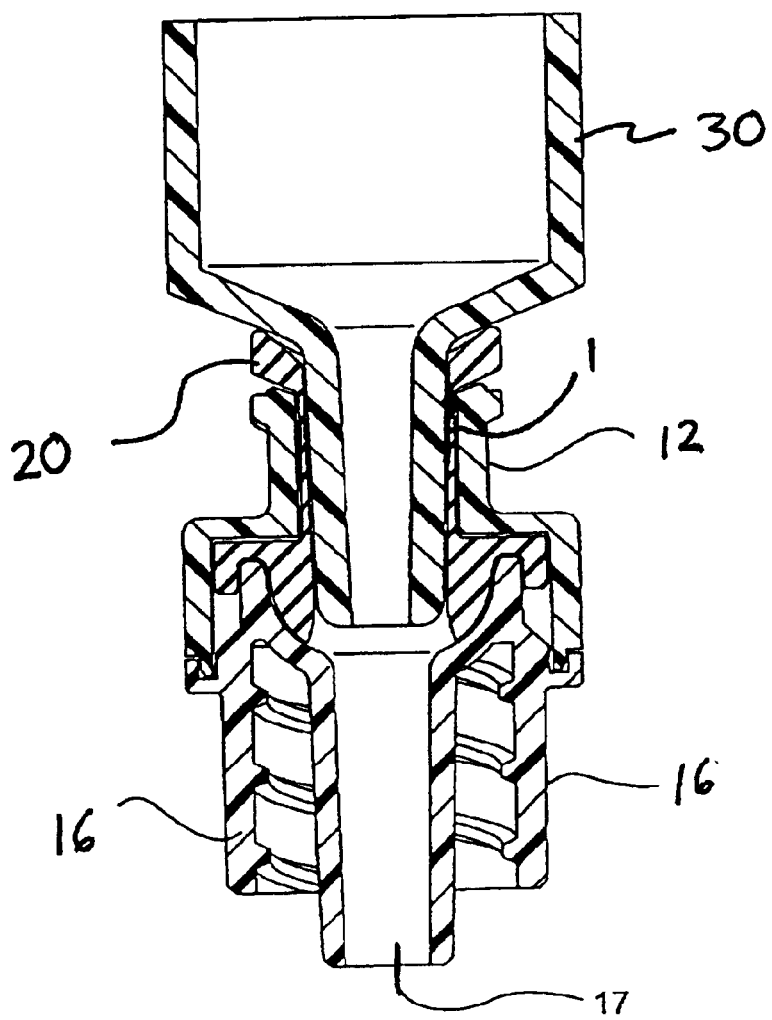
FIG. 2 is a cross sectional view of the needleless luer access connector of FIG. 1 with the male taper of another medical device disposed in the connector so that it is open for fluid flow.
Figure 3:
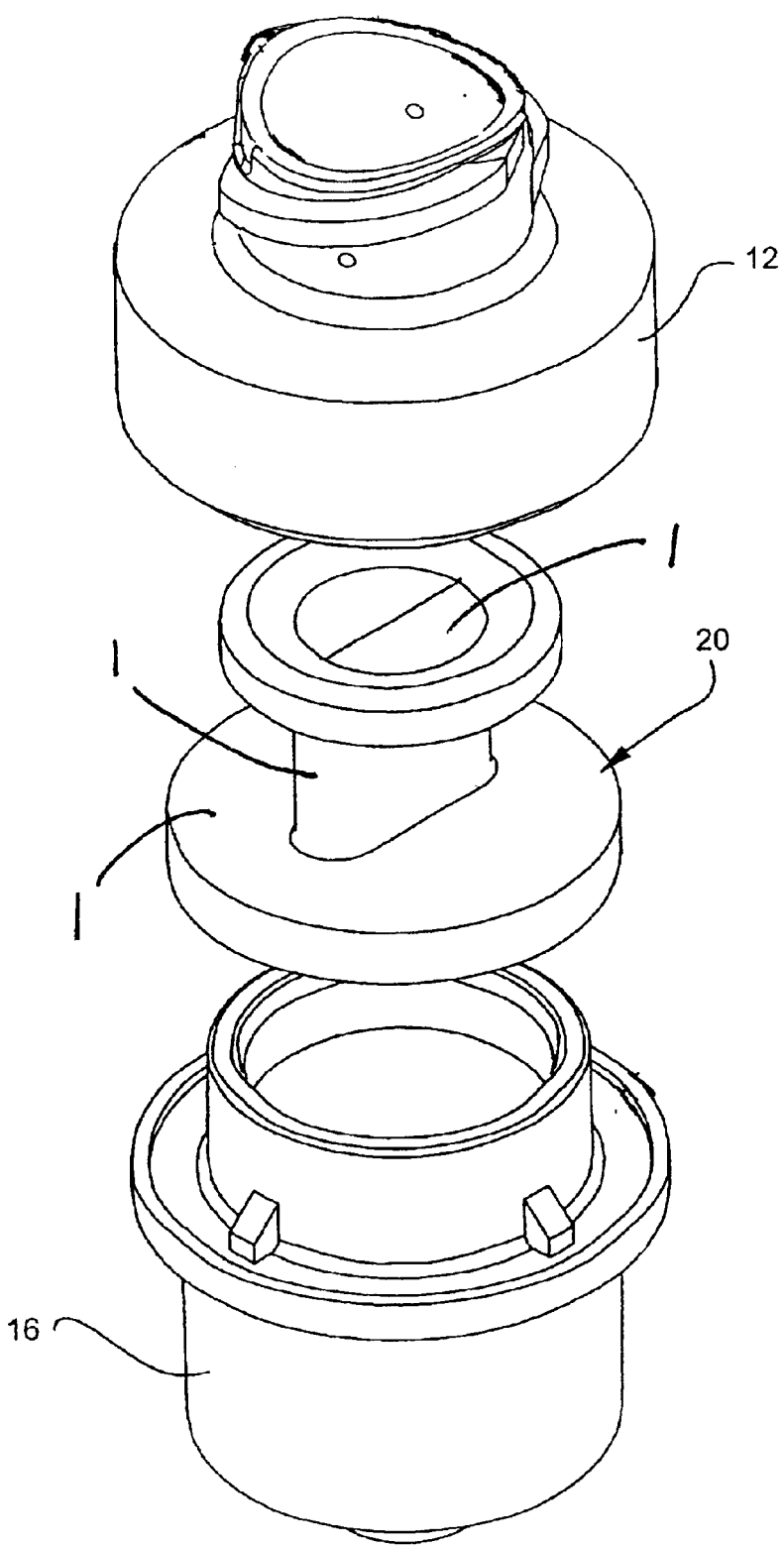
FIG. 3 is an exploded view of a housing, including an elastomeric septum having its exterior surface substantially completely coated with the coating of the instant invention.

Referring to FIGS. 1 and 2, the coating 1 of the instant invention may be applied to the septum 20 of a needleless luer access connector 100. The connector includes a housing 10 having a top portion 12 and a bottom portion 16 that are operably engaged to secure the septum in place on the connector. A central bore 17 extends through the housing, creating a fluid flow path through the housing. This flow path is selectively blocked by the septum, as discussed more fully below. It will be appreciated that the top portion and the bottom portion may have various structures to secure the septum. Further, adhesives or other mechanical structures and techniques may be employed to maintain the septum in place during operation.

As shown in FIG. 1, the septum 20 is in the closed position. The septum includes a slit 21 extending from the top of the septum completely through to the bottom of the septum. The structure of the septum cooperates with the structure of the housing 10, particularly the structure of the top portion 12, to maintain the slit in a sealed condition until operated upon. Consequently, fluids, such as blood and the like, are prevented from passing through the bore 17 of the housing.

In operation, a male luer fitting 30 is inserted into the slit 21 of the septum 20. See FIG. 2. The fitting engages the top surface 13 of the septum, forcing it downward in the top portion 12 and into the bottom portion 16 of the housing 10. The septum deforms as the luer fitting enters the slit, flexing against the inner walls of the top portion. During insertion of the luer fitting, the fitting itself must slide over the top surface of the septum, deforming the elastomeric top surface to create a lead-in that feeds into the slit. Depending on the specific structure and materials of the septum, the fitting itself may also need to slide along the walls that form the slit. During this sliding motion, when no coating is in place, friction between the fitting and the septum may require substantial force by the caregiver. In contrast, the male luer fitting 30 slides easily over the surface of the coating 1. Thus, this force is reduced by applying the coating of the instant invention.

In one implementation of the instant invention, the coating 1 is applied only to the top surface 13 of the septum 20 (see FIG. 1). As discussed below, however, in view of the manufacturing process employed to apply the coating, the coating of the instant invention may also be applied in a substantially continuous layer (that is, with no or a minimum of pinholes formed in the layer) to the entire exterior surface of the septum (see FIG. 3). The coating is preferably applied with a substantially consistent thickness across the top surface. It will be appreciated that the coating could also be applied to the interior walls of the slit 21 but this may affect the integrity of the seal and thus is not most preferred. Further, it will be appreciated that the coating may be applied to only portions of the top surface and still reduce the frictional forces between the luer fitting and the septum. However, it is believed that such an implementation of the instant invention would result in a less effective friction reduction, higher manufacturing cost and a less consistent "feel" to the caregiver and thus would be less desirable.

The lubricious coating of this invention is preferably any one of several polymer coatings that can be securely applied to the surface of a medical device. Examples of such a lubricious polymer coating include di-paraxylene, poly-(p-xylene), polyvinylpyrrolidone, and polytetrafluoroethylene. Further, it is currently most preferred that the material for the coating be parylene-N. Parylene-C and parylene-D may also be employed and practice the invention. These lubricious polymer coatings are preferably polymerized in place on the surface to be treated by vapor deposition, which bonds the polymer coating to the surface of the medical device. In this manner it is possible to establish more reproducible performance over time. Moreover, a coating which is bonded in place will simply last longer and is much less likely to be removed during operation of the medical device. Furthermore, the lubricious polymer coatings of this invention are capable of withstanding the environment in which the medical device is designed to operate and can withstand numerous applications of an alcohol swab. This important since the surface of the flexible portion of the medical device may be swabbed with alcohol prior to each use in order to prevent contaminants from entering the medical device. These lubricious polymer coatings are lipid resistant and generally resistant to other materials typically encountered in medical application.

In one implementation of the invention, parylene-N, which is based on di-paraxylene, is applied using vapor deposition to a septum is made of an elastomeric material, such as silicone or latex. This coating effectively increases the hardness of the elastomeric surface. After forming the septum (but before forming the slit—that is, the septum is "unslit"), the septum may be post cured at elevated temperatures to draw out any volatiles that might interfere with the coating process. The septum is then cleaned, such as by rinsing in alcohol, and allowed to dry. The cleaned septum is placed in a high vacuum environment, such as by resting it in a rotating wire basket within a vacuum chamber. Gaseous monomers of para-xylene are introduced into the environment. These monomers react, spontaneously bonding on the exterior surface of the septum without need for a catalyst. The septum is rotated within the environment to ensure even, complete coating. The coating may be applied using the parylene—gas phase coating process commercially available from Specialty Coating Systems of Indianapolis, Indiana. The coating may also be applied to the elastomeric surface using other techniques, such as by dip coating or spraying the elastomeric surface in the coating material, and then polymerizing the material onto the surface, such as by application of ultraviolet light, radiation and so forth or by employing in situ polymerization as seen with inter penetrating polymer networks. Once the coating has bonded onto the septum, the slit is formed in the septum, such as by slitting the septum with a knife blade, or the like.

Application of parylene can result in a very thin, transparent and pinhole-free film that is applied to substrates in a vacuum chamber by means of vapor deposition. There is no liquid phase, and the process does not involve solvents, catalysts or other environmentally restricted materials. Thus, a highly functional surface coating is provided. To apply the coating only to the top surface, the other portions of the septum would need to be masked to prevent the parylene coating from accessing those surfaces. Of course, other techniques can be employed to apply the parylene coating, either to the full exterior of the septum or to the top surface.

The thickness of the coating can be adjusted by increasing or decreasing the time that the septum spends in the vacuum chamber. The coating may have a thickness between 0.2 and 1.0 microns. Preferably, the coating has a thickness of 0.5 and 0.9 microns, with about 0.79 microns (that is, 0.79 microns +/−0.09 microns) being preferred. Parylene-N has been used as a lubricious coating but not at the thickness used in the instant invention. In particular, certain applicators of parylene coatings recommend applying parylene-N in thicknesses no less than 2.0 microns.

Since the lubricious polymer coating is to be used on the surface of a flexible portion of a medical device, such as a flexible portion formed from silicone, film elasticity and surface adhesion integrity of the lubricious polymer coating are necessary. These characteristics enable the coating to accommodate elongation of the underlying silicone material of the medical device without fracture or loss of the film-to-substrate bond. It has been surprisingly found that a thin lubricant coating in the range of from about 0.5 microns to about 1.0 microns in thickness that is provided on silicone having a Shore A hardness of 50 provides sufficient lubricity and has sufficient flexibility to prevent fracture of the coating. Preferably, a coating in the range of from about 0.5 microns to about 0.9 microns in thickness is used for most medical applications. Parylene is preferably used as the lubricant because it has a typical elongation to break performance of 200%. In addition, parylene is lubricious and tends to eliminate surface tact and stickiness without adding stiffness.

Testing has been performed on certain embodiments of the present invention. Various elastomeric septums were coated with lubricious polymer coatings within the scope of the present invention. The coatings had a thickness of about 1 microns, that is, between 0.9 and 1.1 microns. Once the coating was applied and the septum inserted into a needleless access valve, tests were performed. Conventional syringes where repeatedly inserted into the device. Various characteristics were measured including the force necessary to insert the syringe, the back pressure that the septum could withstand, and the durability of the device in terms of cycles to failure. Table I presents representative data obtained.

TABLE I

| Material of Flexible Portion of Medical Device | Lubricant for Coating | Insertion Force in pounds | Back Pressure in psi. | Durability in cycles to failure |
| --- | --- | --- | --- | --- |
| Polyisoprene | Parylene | 8.7512 | 60.00 | 420 |
| Silicone | Parylene | 6.0360 | 56.00 | 80 |
| Silicone | Parylene | 5.5622 | 42.50 | 51 |
| Silicone | Parylene | 6.1661 | 40.17 | 120 |
| Silicone | Parylene | 8.0237 | 60.00 | 80 |
| Polyisoprene | Parylene | 9.7633 | 55.45 | 211.5 |

It will be appreciated from Table I that all of the embodiments for which data is presented provided acceptable results. It is preferable that the insertion pressure for medical devices inserted into the valve remain below approximately 10 pounds. In most medical applications it is desired that the valve withstand back pressure of at least 20 psi. It is also desirable to have a valve that will operate over the expected life of an IV set or the like. Each of the embodiments of the invention set forth above performs above the necessary level in each tested characteristic.

Additional testing has been performed which found that coatings formed of parylene-N as thin as 0.2 microns up to a thickness of 1.0 microns applied to elastomeric septums made of silicon resulted in favorable friction-reduction characteristics. In certain circumstances, coatings having thicknesses above 1.0 micron were susceptible to flaking off of the septum. It is believed that coatings thinner than 0.2 microns would not result in coatings having appropriate consistency across the top surface of the septum.

It will be understood that other materials may be employed and still practice the invention. In particular, any hydrophobic, hydrophilic, aliphatic or aromatic polymer or hydrocarbon may be employed as the coating material. Certain such materials, such as polyethylene and polypropylene, may be applied to the septum in solution, not in a vapor state. Additionally, the coating material may be polytetrafluoroethylene, other fluorocarbons, and fully or partially pyrolized organic films. Preferably, the slit in the septum is still made after the coating is applied.

Thus it is seen that a lubrication system is provided that may be used on flexible portions of medical devices to minimize friction. Such a lubrication system includes a lubricant that is able to move when the flexible portion flexes, that is biocompatible and is not degraded by application of alcohol or other conventional medical sterilizing and cleaning agents that are typically used with medical devices.

The foregoing specification is intended as illustrative and is not to be taken as limiting the scope of the invention, which is defined by the following claims.

We claim:

1. A lubricious coating for a medical device having a flexible surface, the coating comprising a substantially continuous layer of polymeric material on the flexible surface of the medical device, the layer having a thickness between 0.5 microns and 0.9 microns, wherein the polymeric material is polymerized by vapor deposition and wherein the polymeric material is parylene-N.

2. The lubricious coating of claim 1 wherein the medical device is an elastomeric septum and wherein the coating completely covers the exterior surface of the septum.

3. The lubricious coating of claim 1 wherein the medical device is a septum and wherein the coating covers only a top surface of the septum.

4. A lubricious coating for a medical device having a flexible surface comprising a layer of polymeric material on the flexible surface of the medical device having a thickness between 0.2 and 1.0 microns.

5. The lubricious coating of claim 4 wherein the polymeric material is hydrophobic, hydrophilic, aliphatic or aromatic.

6. The lubricious coating of claim 5 wherein the polymeric material has a thickness between 0.5 and 0.9 microns.

7. The lubricious coating of claim 6 wherein the polymeric material has a thickness of about 0.79 microns.

8. The lubricious coating of claim 6 wherein the polymeric material is polymerized by vapor deposition.

9. The lubricious coating of claim 8 wherein the polymeric material is one of the group of di-paraxylene, poly-(p-xylene), polyvinylpyrrolidone, and polytetrafluoroethylene.

10. The lubricious coating of claim 4 wherein the polymeric material is parylene-N.

11. The lubricious coating of claim 4 wherein the polymeric material is one of the group of parylene-C or parylene-D.

12. The lubricious coating of claim 4 wherein the polymeric material is one of the group of a fluorocarbon or a pyrolized polymer film.

13. A lubricious coating for a septum used in a needleless luer access connector, the septum having at least one flexible surface, the coating comprising a substantially continuous layer of polymeric material on the at least one flexible surface of the medical device, the layer having a thickness between 0.2 and 1.0 microns, and wherein the polymeric material is one of the group of di-paraxylene, poly-(p-xylene), polyvinylpyrrolidone, and polytetrafluoroethylene.

14. The lubricious coating of claim 13 wherein the coating covers the entire exterior surface of the septum and wherein the septum is unslit.

15. The lubricious coating of claim 13 wherein the septum has a top surface and the coating covers only the top surface.

16. The lubricious coating of claim 13 wherein the layer has a thickness between 0.5 and 0.9 microns.

17. The lubricious coating of claim 13 wherein the material is parylene-N.

18. The lubricious coating of claim 16 wherein the material is parylene-N.

19. The lubricious coating of claim 17 wherein the coating covers the entire exterior surface of the septum.

20. The lubricious coating of claim 13 wherein the material is parylene-N, the layer has a thickness about 0.79 microns, the coating covers the entire exterior surface of the septum and the septum is unslit.

* * * * *